United States Patent [19]

Motoyama et al.

[11] Patent Number: 5,932,759

[45] Date of Patent: Aug. 3, 1999

[54] PROCESS FOR PRODUCING SUBSTITUTED AMINES AND A METHOD FOR PURIFYING SYNTHETIC INTERMEDIATES THEREFOR

[75] Inventors: Yoshio Motoyama; Naoshi Nagai; Takeshi Ishitoku; Noriaki Kihara, all of Yamaguchi-ken, Japan

[73] Assignee: Mitsui Chemicals, Inc., Tokyo, Japan

[21] Appl. No.: 08/800,149

[22] Filed: Feb. 13, 1997

Related U.S. Application Data

[63] Continuation of application No. 08/422,782, Apr. 17, 1995, abandoned.

[30] Foreign Application Priority Data

| Apr. 22, 1994 | [JP] | Japan | 6-084979 |
| Feb. 2, 1995 | [JP] | Japan | 7-016178 |
| Feb. 3, 1995 | [JP] | Japan | 7-017232 |

[51] Int. Cl.$^6$ .................................. C07C 261/00
[52] U.S. Cl. .................. 560/160; 560/312; 564/300; 564/301
[58] Field of Search .................. 564/300, 301; 560/312, 160

[56] References Cited

U.S. PATENT DOCUMENTS

| 3,230,260 | 1/1966 | Snyder . | |
| 5,008,455 | 4/1991 | Nakajima | 564/300 |
| 5,075,504 | 12/1991 | Schneider | 564/301 |
| 5,166,436 | 11/1992 | Lee | 564/301 |
| 5,382,685 | 1/1995 | Klein | 564/301 |
| 5,393,921 | 2/1995 | Lazar | 562/512 |
| 5,488,162 | 1/1996 | Buckland | 564/301 |

FOREIGN PATENT DOCUMENTS

| 103895 | 3/1984 | European Pat. Off. | 564/301 |
| 0341693 | 11/1989 | European Pat. Off. . | |
| 0581613 | 2/1994 | European Pat. Off. . | |
| 0581613A1 | 2/1994 | European Pat. Off. . | |
| 1377470 | 9/1964 | France . | |
| 3245503 | 6/1984 | Germany . | |
| 58-167546 | 10/1983 | Japan | 560/312 |
| 1064482 | 4/1967 | United Kingdom . | |

OTHER PUBLICATIONS

Brady et al., Journal of the Chemical Society (1930), The Ralph Forster Laboratories of Organic Chemistry, University College, London, The Isomerism of the Oximes, Part XXXVII, pp. 226–229.

Goel et al., Organic Preparations and Procedures International, vol. 19, No. 1 (1987).

Buehler, Journal of Organic Chemistry, vol. 32, pp. 261–265 (1967).

*Primary Examiner*—Michael L. Shippen
*Attorney, Agent, or Firm*—Birch, Stewart, Kolasch & Birch, LLP

[57] ABSTRACT

The present invention relates to a process for producing a substituted amine represented by the general formula (IV):

$$R^2NHOR^3 \quad (IV)$$

(wherein $R^2$ represents a hydrogen atom, a hydrocarbon group or a heteroatom-containing hydrocarbon group, and $R^3$ represents a hydrocarbon group or a heteroatom-containing hydrocarbon group), which comprises the steps of:

(b) reacting a hydroxamic acid represented by the general formula (II):

$$R^1CONHOH \quad (II)$$

(wherein $R^1$ represents a hydrogen atom or a hydrocarbon group) in the presence of a base with a reaction reagent capable of introducing a hydrocarbon or a heteroatom-containing hydrocarbon group to an oxygen atom and/or a nitrogen atom to form a substituted hydroxamic acid represented by the general formula (III):

$$\underset{R^2}{R^1CONOR^3} \quad (III)$$

(wherein $R^1$, $R^2$ and $R^3$ possess the same meanings as defined above), (c) hydrolyzing said substituted hydroxamic acid (III) in the presence of a base or an acid to produce a substituted amine represented by the general formula (IV):

$$R^2NHOR^3 \quad (IV)$$

(wherein $R^2$ and $R^3$ possess the same meanings as defined above). The present further relates to a method for purifying a synthetic intermediate for said substituted amine.

14 Claims, No Drawings

PROCESS FOR PRODUCING SUBSTITUTED AMINES AND A METHOD FOR PURIFYING SYNTHETIC INTERMEDIATES THEREFOR

This application is a continuation of application Ser. No. 08/422,782 filed on Apr. 17, 1995, now abandoned.

BACKGROUND OF THE INVENTION

1. Field of the Invention

The present invention relates to a process for producing substituted amines useful as synthetic intermediates for medicine and agricultural chemicals as well as to a method for purifying synthetic intermediates therefor.

2. Description of the Prior Art

Generally, a process for producing alkoxyalkylamines from hydroxylamine or a salt thereof involves reaction of a chloroformate with a hydroxylamine salt in the presence of sodium hydroxide and subsequent alkylation with a dialkyl sulfate in the presence of sodium hydroxide, followed by hydrolysis.

For example, a process for producing methoxymethylamine is known as described in Org. Prep. Proced., 19, 75 (1987). In this prior art process, hydroxylamine hydrochloride is allowed to react with ethyl chloroformate in an aqueous solution of sodium hydroxide to form ethyl hydroxycarbamate which is then dimethylated with dimethyl sulfate in an aqueous solution of sodium hydroxide, followed by hydrolysis with hydrochloric acid, whereby methoxymethylamine hydrochloride is obtained in 70% yield.

DE3245503 discloses a process for producing methoxymethylamine via butyl N,O-dimethylcarbamate as an intermediate. According to this prior art process, the starting material hydroxylamine sulfate is allowed to react with butyl chloroformate in the presence of sodium hydroxide to form butyl hydroxycarbamate which is then subjected to the steps of extraction with dichloromethane and of drying, and after the solvent is distilled off, said butyl hydroxycarbamate is dimethylated with dimethyl sulfate in an aqueous solution of sodium hydroxide, followed by hydrolysis with hydrochloric acid, whereby methoxymethylamine hydrochloride is obtained in 65% yield.

With respect to the synthesis of hydroxamic acids, conventional processes involve reaction of carboxylates with hydroxylamine or a salt thereof, or reaction of acid halides or acid anhydrides with hydroxylamine or a salt thereof (EP306936, An. Quim., 72, 683 (1976), ZL. Prikl. khim., 45, 1895 (1972), "Kagaku Daijiten" (Encyclopedic Dictionary of Chemistry) published by Tokyo Kagaku Dojin K. K.). However, there is no suggestion of conversion of the resulting hydroxamic acids into alkoxyalkylamines.

The prior art processes with chloroformates as the starting material have the problem that the yield of the product, alkoxyalkylamines, is too low for applicability in industry.

With respect to the production of alkoxyamines, the following 3 processes are known:

(1) A process in which benzaldoxime obtained by reacting benzaldehyde with hydroxylamine is O-alkylated with an alkylating agent and then hydrolyzed (J. Org. Chem., 32, 261 (1967));

(2) A process in which hydroxylamine disulfonate is O-alkylated with an alkylating agent and then hydrolyzed (Berichte, 53, 1477 (1920)); and (3) A process in which hydroxylamine-O-sulfonic acid is methoxylated with sodium methoxide (EU Pat. 0341693).

Of these 3 processes already reported, the process (1) has the disadvantage of the low yield of the product because of the occurrence of N-alkylation of benzaldoxime that proceeds competitively with O-alkylation. The process (2) has the disadvantage that a large amount of inorganic waste is discharged as a source of environmental pollution. The process (3) has the disadvantage that the production cost is raised by the use of expensive hydroxylamine-O-sulfonic acid.

Conventional processes for producing N,O-dimethylhydroxylamine involve conversion of hydroxylamine into hydroxycarbamate and subsequent dimethylation thereof, followed by decarboalkoxylation (Japanese Laid-Open Patent Publication No. 56757/1994) or reaction of nitrite, bisulfite and $SO_2$ to form sulfonimide from which N,O-dimethylhydroxylamine is obtained (FR Patent Publication No. 1377470 A (Laid Open)). Of these processes, the process described in FR Patent Publication No. 1377470 A is disadvantageous as an industrial process because of the discharge of a large amount of waste liquid, while the process described in Japanese Laid-Open Patent Publication No. 56757/1994 cannot be said an effective process because of the environmental pollution and high production costs resulting from the step of extracting an intermediate, N,O-dimethylhydroxycarbamate, with an organic solvent such as halogenated hydrocarbons. Furthermore, since this step brings about simultaneous extraction of O-methylhydroxycarbamate formed as by-product during the formation of N,O-dimethylhydroxycarbamate, there results the contamination of N,O-dimethylhydroxylamine with O-methylhydroxylamine after deprotection. The close boiling points of the two compounds (42.3° C. for N,O-dimethylhydroxylamine and 48.1° C. for O-methylhydroxylamine) make their purification through distillation very difficult, and therefore their separation requires multistage distillation columns.

U.S. Pat. No. 3,230,260 discloses a method for purifying a final product N,O-dimethylhydroxylamine, in which formaldehyde is added at pH 7 or less to O-methylhydroxylamine contained in N,O-dimethylhydroxylamine to convert it into gaseous O-methylformaldehydeoxime so that O-methylhydroxylamine can be removed.

However, the removal of O-methylhydroxylamine in the method described in U.S. Pat. No. 3,230,260 must undergo the complicated steps of extracting with an organic solvent such as halogenated hydrocarbons etc. an intermediate N,O-dimethylhydroxamic acid and by-products including O-methylhydroxamic acid from an aqueous solution containing inorganic salts etc., concentrating the extraction solvent, deprotecting the products, and adding formaldehyde to convert O-methylhydroxylamine into gaseous O-methylformaldehydeoxime which is then separated. Furthermore, the halogenated hydrocarbon solvent for extraction and formaldehyde for conversion are highly toxic, and in particular, formaldehyde is extremely difficult to handle with its maximum permissible concentration being as low as 2 ppm as specified in the law. Furthermore, the high water-solublity of formaldehyde makes recovery of unreacted formaldehyde difficult. In addition, the recovery of O-methylformaldehydeoxime formed requires facilities of high cooling efficiency because of its low boiling point (−12° C.), and therefore the facilities and the complicated procedures cost much.

OBJECTS AND SUMMARY OF THE INVENTION

The first object of the invention is to provide a process for producing a substituted amine in high yield at low costs with less environmental pollution.

To accomplish this object, the present inventors studied a method of synthesizing a substituted amine, particularly via a hydroxamic acid. As a result, they arrived at a method of selectively monosubstituting or disubstituting the hydroxamic acid with a reaction reagent (e.g. an alkylating agent) capable of introducing a hydrocarbon group or a heteroatom-containing hydrocarbon group onto the oxygen atom and/or the nitrogen atom of the hydroxamic acid, and they further found that hydrolysis of the resulting substituted hydroxamic acid in the presence of a base or an acid can yield the desired substituted amine in high yield.

The second object of the invention is to provide N,O-disubstituted hydroxylamine and/or O-substituted hydroxylamine as final product by separating an intermediate N,O-disubstituted hydroxamic acid (e.g. N,O-dimethylhydroxamic acid) from another intermediate O-substituted hydroxamic acid (e.g. O-methylhydroxamic acid) in an easier and safer manner than the conventional method.

To accomplish this object, the present inventors have, as a result of their eager study of the separation of the N,O-disubstituted hydroxamic acid from the O-substituted hydroxamic acid, found that the N,O-disubstituted hydroxamic acid possess an azeotropic point with water contained in the reaction system, and also that the unreacted reaction reagents and O-substituted hydroxamic acid present in the reaction system are not contained in the N,O-disubstituted hydroxamic acid obtained by direct distillation as an azeotropic distillate.

That is, the present invention encompasses:

(1) A process for producing a substituted amine represented by the general formula (IV):

(wherein $R^2$ represents a hydrogen atom, a hydrocarbon group or a heteroatom-containing hydrocarbon group, and $R^3$ represents a hydrocarbon group or a heteroatom-containing hydrocarbon group), which comprises the steps of:

(b) reacting a hydroxamic acid represented by the general formula (II):

(wherein $R^1$ represents a hydrogen atom or a hydrocarbon group) in the presence of a base with a reaction reagent capable of introducing a hydrocarbon group or a heteroatom-containing hydrocarbon group onto an oxygen atom and/or a nitrogen atom to form a substituted hydroxamic acid represented by the general formula (III):

(III)

(wherein $R^1$, $R^2$ and $R^3$ possess the same meanings as defined above), (c) hydrolyzing said substituted hydroxamic acid (III) in the presence of a base or an acid to produce a substituted amine represented by the general formula (IV):

(wherein $R^2$ and $R^3$ possess the same meanings as defined above).

(2) A process for producing a substituted amine according to item (1), which further comprises the steps of:

(a) reacting hydroxylamine or a salt thereof in the presence of a base with an ester represented by the general formula (I):

(wherein $R^1$ represents a hydrogen atom or a hydrocarbon group, and $R^4$ represents a hydrocarbon group) to produce a reaction mixture containing a hydroxamic acid represented by the general formula (II):

(wherein $R^1$ possesses the same meaning as defined above), (b) reacting said hydroxamic acid-containing reaction mixture without separation of the hydroxamic acid from said mixture, with a reaction reagent capable of introducing a hydrocarbon group or a heteroatom-containing hydrocarbon group onto an oxygen atom and/or a nitrogen atom to produce a substituted hydroxamic acid represented by the general formula (III):

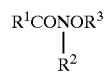
(III)

(wherein $R^1$ possesses the same meaning as defined above, $R^2$ represents a hydrogen atom, a hydrocarbon group or a heteroatom-containing hydrocarbon group, and $R^3$ represents a hydrocarbon group or a heteroatom-containing hydrocarbon group), (c) hydrolyzing said substituted hydroxamic acid (III) in the presence of a base or an acid to produce a substituted amine represented by the general formula (IV):

(wherein $R^2$ and $R^3$ possess the same meanings as defined above).

(3) A process for producing a substituted amine according to item (1), wherein the reaction reagent capable of introducing a hydrocarbon group or a heteroatom-containing hydrocarbon group onto an oxygen atom and/or a nitrogen atom is an alkylating agent, the substituted hydroxamic acid is a N,O-dialkylhydroxamic acid and/or an O-alkylhydroxamic acid, and the substituted amine is an alkoxyalkylamine and/or an alkoxyamine.

(4) A process for producing a substituted amine according to item (1), wherein the substituted hydroxamic acid is a N,O-disubstituted hydroxamic acid represented by the general formula (III-a):

(III-a)

(wherein $R^1$ represents a hydrogen atom or a hydrocarbon group, $R^3$ represents a hydrocarbon group or a heteroatom-containing hydrocarbon group) and said N,O-disubstituted hydroxamic acid is hydrolyzed in the presence of a base or an acid to produce a disubstituted amine represented by the general formula (IV-a):

$$R^3NHOR^3 \quad (IV\text{-}a)$$

(wherein $R^3$ possesses the same meaning as defined above).

(5) A process for producing a substituted amine according to item (4), wherein the reaction reagent capable of introducing a hydrocarbon group or a heteroatom-containing hydrocarbon group onto an oxygen atom and/or a nitrogen atom is an alkylating agent, the N,O-disubstituted hydroxamic acid is a N,O-dialkylhydroxamic acid, and the disubstituted amine obtained by hydrolysis thereof is an alkoxyalkylamine.

(6) A process for producing a substituted amine according to item (1), wherein the substituted hydroxamic acid is an O-substituted hydroxamic acid represented by the general formula (III-b):

$$R^1CONHOR^3 \quad (III\text{-}b)$$

(wherein $R^1$ represents a hydrogen atom or a hydrocarbon group, $R^3$ represents a hydrocarbon group or a heteroatom-containing hydrocarbon group) and said O-substituted hydroxamic acid is hydrolyzed in the presence of a base or an acid to produce a monosubstituted amine represented by the general formula (IV-b):

$$H_2NOR^3 \quad (IV\text{-}b)$$

(wherein $R^3$ possesses the same meaning as defined above).

(7) A process for producing a substituted amine according to item (6), wherein the reaction reagent capable of introducing a hydrocarbon group or a heteroatom-containing hydrocarbon group onto an oxygen atom and/or a nitrogen atom is an alkylating agent, the O-substituted hydroxamic acid is an O-alkylhydroxamic acid, and the monosubstituted amine obtained by hydrolysis thereof is an alkoxyamine.

(8) A process for producing a substituted amine according to item (1), which comprises the steps of:

(a) reacting hydroxylamine or a salt thereof in the presence of a base with an ester represented by the general formula (I):

$$R^1COOR^4 \quad (I)$$

(wherein $R^1$ represents a hydrogen atom or a hydrocarbon group, and $R^4$ represents a hydrocarbon group) to produce a reaction mixture containing a hydroxamic acid represented by the general formula (II):

$$R^1CONHOH \quad (II)$$

(wherein $R^1$ possesses the same meaning as defined above), (b) reacting said hydroxamic acid-containing reaction mixture in the presence of a base without separation of the hydroxamic acid from said mixture, with an alkylating agent at the molar ratio of the alkylating agent to hydroxylamine or a salt thereof being from 2 to 4 (which, in the case of the salt, is calculated not from the number of moles of the salt itself but from the number of moles of hydroxylamine contained in said salt), to produce a N,O-dialkylhydroxamic acid represented by the general formula (III-a'):

(wherein $R^1$ possesses the same meaning as defined above, and $R^{3'}$ represents an alkyl group), (c) hydrolyzing said N,O-dialkylhydroxamic acid in the presence of a base or an acid to produce an alkoxyalkylamine represented by the general formula (IV-a'):

$$R^{3'}NHOR^{3'} \quad (IV\text{-}a')$$

(wherein $R^{3'}$ possesses the same meaning as defined above).

(9) A process for producing a substituted amine according to item (1), which comprises the steps of:

(a) reacting hydroxylamine or a salt thereof in the presence of a base with an ester represented by the general formula (I):

$$R^1COOR^4 \quad (I)$$

(wherein $R^1$ represents a hydrogen atom or a hydrocarbon group, and $R^4$ represents a hydrocarbon group) to produce a reaction mixture containing a hydroxamic acid represented by the general formula (II):

$$R^1CONHOH \quad (II)$$

(wherein $R^1$ possesses the same meaning as defined above), (b) reacting said hydroxamic acid-containing reaction mixture in the presence of a base without separation of the hydroxamic acid from said mixture, with an alkylating agent at the molar ratio of the alkylating agent to hydroxylamine or a salt thereof being from 0.5 to 1.5 (which, in the case of the salt, is calculated not from the number of moles of the salt itself but from the number of moles of hydroxylamine contained in said salt), to produce an O-alkylhydroxamic acid represented by the general formula (III-b'):

$$R^1CONHOR^{3'} \quad (III\text{-}b')$$

(wherein $R^1$ possesses the same meaning as defined above, and $R^{3'}$ represents an alkyl group), (c) hydrolyzing said O-alkylhydroxamic acid in the presence of a base or an acid to produce an alkoxyalkylamine represented by the general formula (IV-b'):

$$H_2NOR^{3'} \quad (IV\text{-}b')$$

(wherein $R^{3'}$ possesses the same meaning as defined above).

(10) A process for producing a substituted amine according to item (1), wherein the mixture containing a substituted hydroxamic acid represented by the general formula (III):

(wherein $R^1$ possesses the same meaning as defined above, $R^2$ represents a hydrogen atom, a hydrocarbon group or a heteroatom-containing hydrocarbon group, and $R^3$ represents a hydrocarbon group or a heteroatom-containing hydrocarbon group) is distilled with water to separate a N,O-disubstituted hydroxamic acid represented by the general formula (III-a):

$$R^1CONOR^3 \atop | \atop R^3 \qquad \text{(III-a)}$$

(wherein $R^1$ and $R^3$ possess the same meanings as defined above) as an azeotropic distillate with water from said mixture, and said N,O-disubstituted hydroxamic acid is hydrolyzed in the presence of a base or an acid to produce a disubstituted amine represented by the general formula (IV-a):

$$R^3NHOR^3 \qquad \text{(IV-a)}$$

(wherein $R^3$ possesses the same meaning as defined above).

(11) A process for producing a substituted amine according to item (1), wherein the mixture containing a substituted hydroxamic acid represented by the general formula (III):

$$R^1CONOR^3 \atop | \atop R^2 \qquad \text{(III)}$$

(wherein $R^1$ possesses the same meaning as defined above, $R^2$ represents a hydrogen atom, a hydrocarbon group or a heteroatom-containing hydrocarbon group, and $R^3$ represents a hydrocarbon group or a heteroatom-containing hydrocarbon group) is distilled with water to separate a N,O-disubstituted hydroxamic acid represented by the general formula (III-a):

$$R^1CONOR^3 \atop | \atop R^3 \qquad \text{(III-a)}$$

(wherein $R^1$ and $R^3$ possess the same meanings as defined above) as an azeotropic distillate with water from said mixture, and a purified O-substituted hydroxamic acid represented by the general formula (III-b):

$$R^1CONHOR^3 \qquad \text{(III-b)}$$

(wherein $R^1$ and $R^3$ possess the same meanings as defined above) is hydrolyzed in the presence of a base or an acid to produce a monosubstituted amine represented by the general formula (IV-b):

$$H_2NOR^3 \qquad \text{(IV-b)}$$

(wherein $R^3$ possesses the same meaning as defined above).

(12) A method for purifying a N,O-disubstituted hydroxamic acid and/or an O-substituted hydroxamic acid, which comprises distilling a mixture containing a N,O-disubstituted hydroxamic acid represented by the general formula (V):

$$R^5CONOR^7 \atop | \atop R^6 \qquad \text{(V)}$$

(wherein $R^5$ represents a hydrogen atom or a hydrocarbon group, and $R^6$ and $R^7$ represent a hydrocarbon group or a heteroatom-containing hydrocarbon group) or a mixture containing said N,O-disubstituted hydroxamic acid and an O-substituted hydroxamic acid represented by the general formula (VI):

$$R^5CONHOR^7 \qquad \text{(VI)}$$

(wherein $R^5$ and $R^7$ possess the same meanings as defined above) is with water to separate said N,O-disubstituted hydroxamic acid as an azeotropic distillate with water from said mixture.

(13) A process according to item (12), wherein the N,O-disubstituted hydroxamic acid is a N,O-dialkylhydroxamic acid represented by the general formula (V'):

$$R^{5'}CONOR^{7'} \atop | \atop R^{6'} \qquad \text{(V')}$$

(wherein $R^{5'}$ represents a hydrogen atom or an alkyl group, and $R^{6'}$ and $R^{7'}$ represent alkyl groups) and the O-substituted hydroxamic acid is an O-alkylhydroxamic acid represented by the general formula (VI'):

$$R^{5'}CONHOR^{7'} \qquad \text{(VI')}$$

(wherein $R^{5'}$ and $R^{7'}$ possess the same meanings as defined above).

(14) A method according to item (13), wherein said N,O-dialkylhydroxamic acid is purified.

(15) A method according to item (13), wherein a mixture containing said N,O-dialkylhydroxamic acid and said O-alkylhydroxamic acid is distilled with water to separate said N,O-dialkylhydroxamic acid as an azeotropic distillate with water from said mixture in order to purify said O-alkylhydroxamic acid.

(16) A method according to any one of items (13) to (15), wherein said N,O-dialkylhydroxamic acid is N,O-dimethylacetohydroxamic acid.

(17) A method according to item (13) or (15), wherein said O-alkylhydroxamic acid is O-methylacetohydroxamic acid.

Examples of hydrocarbons represented by $R^1$, $R^2$, $R^3$ or $R^4$ in the formulae (I), (II), (III) and (IV) are $C_1$–$C_5$ alkyl groups, such as methyl group, ethyl group, n-propyl group, isopropyl group, n-butyl group, isobutyl group, sec-butyl group, tert-butyl group, n-pentyl group, etc.; $C_2$–$C_5$ alkenyl groups, such as allyl group etc.; $C_3$–$C_7$ cycloalkyl groups, such as cyclopropyl group, cyclobutyl group, cyclopentyl group, cyclohexyl group, cycloheptyl group, etc.; aryl groups, such as phenyl group, tolyl group, xylyl group, etc.; aralkyl groups, such as benzyl group, phenethyl group, etc.; and aryl-$C_2$–$C_5$-alkenyl groups, such as 3-phenyl-2-propenyl group etc.

Examples of heteroatom-containing hydrocarbons represented by $R^2$ or $R^3$ in the formulae (III) and (IV) are halogenated hydrocarbons, such as fluoromethyl group, chloromethyl group, 3-chloroallyl group, 4-chlorobenzyl group, etc.; carbonylated alkyl groups, such as carboxymethyl group, ethoxycarbonylmethyl group, 1-carboxy-1-methylethyl group, etc.; and cyanoalkyl groups, such as cyanomethyl group, cyanoethyl group, etc.

Although the hydroxamic acid of the above formula (II) used in the present invention can be produced by reacting a carboxylate with hydroxylamine or a salt thereof or by reacting an acid halide or acid anhydride with hydroxylamine or a salt thereof, the reaction of an ester of the above formula (I) with hydroxylamine or a salt thereof in the presence of a base is preferred for production of hydroxamic acid (II) in consideration of its yield.

Hydroxylamine or a salt thereof used in the invention includes e.g. hydroxylamine, hydroxylamine sulfate, hydroxylamine hydrochloride and hydroxylamine oxalate, among which hydroxylamine sulfate and hydroxylamine hydrochloride are particularly preferable because of their stability and reasonable price. Hydroxylamine or a salt thereof may be in solution including an aqueous solution, a methanol solution, etc.

The ester represented by the above formula (I) includes e.g. methyl formate, ethyl formate, methyl acetate, ethyl acetate, n-propyl acetate, n-butyl acetate, isobutyl acetate, phenyl acetate, methyl propionate, ethyl propionate, methyl butyrate, ethyl butyrate, methyl isovalerate, ethyl isovalerate, methyl benzoate and ethyl benzoate, among which methyl acetate and ethyl acetate are preferable because of their easy handling and reasonable price.

The base used for production of hydroxamic acids includes e.g. alkali metal or alkaline earth metal hydroxides, typically, sodium hydroxide, potassium hydroxide, lithium hydroxide, cesium hydroxide and barium hydroxide; alkali metal bicarbonates, typically sodium bicarbonate and potassium bicarbonate; alkali metal or alkaline earth metal carbonates, typically, sodium carbonate, potassium carbonate and barium carbonate; aluminates, typically sodium aluminate and potassium aluminate; alkoxides, such as sodium methoxide, sodium ethoxide, potassium t-butoxide, etc., and these bases may be used singly or in combination. Sodium hydroxide is a particularly preferable base because of its reasonable price. Although these bases are preferably used in aqueous solution, they may be used as solid or as a solution in an organic solvent including alcohols etc.

The reaction solvent used for production of hydroxamic acids is preferably water, but it may be an inert organic solvent, for example, ethers such as diethyl ether and tetrahydrofuran, or aromatic compounds such as benzene, toluene, etc., and these solvents may be used singly or in combination, or in a two-layer system.

The molar ratio of the ester (I) to hydroxylamine or a salt thereof is usually 0.2 to 10, preferably 0.5 to 2, more preferably 0.8 to 1.3.

Although the amount of the base used for production of hydroxamic acids is not particularly limited, it is preferably used in such an amount that the reaction solution can be controlled within the pH range described below, and the molar ratio of the base to hydroxylamine or a salt thereof is usually 0.1 to 10, preferably 0.5 to 3.

The starting materials may be added in any order, but it is preferred that a reactor is charged first with hydroxylamine or a salt thereof and the reaction solvent, and then with the ester (I) with which a base is added successively or simultaneously so that the reaction temperature and the pH of the reaction solution can be controlled within predetermined ranges. When hydroxylamine sulfate or hydrochloride is used as starting materials, a base is preferably added to neutralize said salt before introduction of the ester (I).

The reaction temperature adopted for production of hydroxamic acids is usually −20 or 80° C., preferably −10 to 40° C., more preferably 0 to 25° C. For this reaction, the pH range is usually pH 7 to 14, preferably pH 9 to 14, more preferably pH 10 to 13.

The hydroxamic acid (II) thus obtained may be isolated or may be subjected to further reaction in situ without isolation with a reaction reagent capable of introducing a hydrocarbon group or a heteroatom-containing hydrocarbon group onto an oxygen atom/or a nitrogen atom. In consideration of the post-treatment and costs for the subsequent extraction, the hydroxamic acid is preferably subjected to the subsequent reaction in situ without subjecting it to an isolation step.

If the isolated hydroxamic acid (II) is to be used, the same base and reaction solvent as in the production of the hydroxamic acid can be used for reaction with the reaction reagent capable of introducing a hydrocarbon group or a heteroatom-containing hydrocarbon group onto an oxygen atom/or a nitrogen atom.

The reaction reagent capable of introducing a hydrocarbon group or a heteroatom-containing hydrocarbon group onto an oxygen atom and/or a nitrogen atom includes alkylating agents, such as dialkyl sulfates, typically dimethyl sulfate and diethyl sulfate; hydrocarbon chlorides, typically, methyl chloride, fluorochloromethane, bromochloromethane, ethyl chloride, propyl chloride, isopropyl chloride, allyl chloride, 1,3-dichloropropen, 4-chlorobenzyl chloride and butyl chloride; hydrocarbon bromides, typically, methyl bromide, ethyl bromide, propyl bromide, isopropyl bromide, allyl bromide and butyl bromide; hydrocarbon iodides, typically, methyl iodide, ethyl iodide, propyl iodide, isopropyl iodide, allyl iodide and butyl iodide, as well as halogenated carbonyl compounds, typically, 1-chloroacetic acid, ethyl 1-chloroacetate, ethyl 1-bromoacetate and 2-chloroisobutyric acid, and halogenated nitriles, typically chloroacetonitrile and 3-bromopropionitrile.

If the hydroxamic acid (II) is to be subjected without isolation to further reaction with the reaction reagents (e.g. an alkylating agent) for preparation of N,O-disubstituted hydroxamic acid as desired intermediate, such as N,O-dialkylhydroxamic acid etc., the molar ratio of the reaction reagents (including an alkylating agent etc.) to hydroxylamine or a salt thereof is usually 2 or more, preferably 2 to 4, more preferably 2 to 2.5 (which, in the case of the salt, is calculated not from the number of moles of the salt itself but from the number of moles of hydroxylamine contained in said salt; Hereinafter the same).

If the desired intermediate is an O-substituted hydroxamic acid such as O-alkylhydroxamic acid etc., the molar ratio of the reaction reagents (including an alkylating agent etc.) to hydroxylamine or a salt thereof is usually 0.5 to 1.5, preferably 0.9 to 1.2.

Although the amount of the base used for reaction of the hydroxamic acid (II) with the reaction reagents including an alkylating agent is not particularly limited, it is preferably used in such an amount that the reaction solution can be controlled within the pH range described below. If the hydroxamic acid (II) is subjected to further reaction without isolation, the molar ratio of the base to hydroxylamine or a salt thereof is usually 0.1 to 10, preferably 0.5 to 3.

The reaction reagents e.g. an alkylating agent etc. and the base may be added in any order, but the base is preferably introduced simultaneously with the reaction reagents to control the reaction temperature and the pH of the reaction solution within predetermined ranges. In this step, the reaction temperature is usually −20 to 80° C., preferably −10 to 40° C., more preferably 0 to 25° C. and the pH range of the reaction solution is usually pH 7 to 14, preferably pH 9 to 14, more preferably pH 10 to 14. Where the reaction reagents including an alkylating agent etc. turn gaseous under the reaction conditions, the reaction must be carried out under pressure.

The O-substituted hydroxamic acid (III-b) can be formed as by-product where the desired intermediate is the N,O-disubstituted hydroxamic acid (III-a), and the N,O-disubstituted hydroxamic acid (III-a) can be formed as by-product where the desired intermediate is the O-substituted hydroxamic acid (III-b). However, the N,O-disubstituted hydroxamic acid (III-a) possesses an azeotropic point with water and is easy to separate from the aqueous reaction solution with aromatic hydrocarbons as extraction solvent, such as toluene, xylene, etc., whereas the O-substituted hydroxamic acid (III-b) is difficult to extract from the aqueous reaction solution with said aromatic hydrocarbons and also hard to distill azeotropically with water. Hence, said two hydroxamic acids can be separated almost completely from each other by extraction of the N,O-disubstituted hydroxamic acid (III-a) with said aromatic hydrocarbons, or by azeotropic distillation with water under reduced pressure.

Where the desired intermediate is the N,O-disubstituted hydroxamic acid (III-a), it is usually separated from the reaction system by distillation etc. and then subjected to hydrolysis.

Where the desired intermediate is the O-substituted hydroxamic acid (III-b), it may be isolated or may be subjected to the subsequent step of hydrolysis in situ without isolation. For the elimination of post-treatment and the reduction in costs for extraction solvent, the intermediate is preferably subjected to hydrolysis in situ without isolation. In the case of extraction, the solvent used includes alcohols such as isopropanol, isobutanol, etc., ethers such as diethyl ether, tetrahydrofuran, etc., halogenated hydrocarbons such as chloroform, dichloromethane, dichloroethane, etc., and nitriles such as acetonitrile etc., among which isopropanol, dichloromethane and dichloroethane are preferably used for their extraction efficiency and reasonable costs.

The base used for hydrolysis of substituted hydroxamic acid (III) includes hydroxides, carbonates, etc., of alkali metals such as lithium, sodium, potassium, etc.; hydroxides, carbonates, etc., of alkaline earth metals such as magnesium, calcium, barium, etc.; organic bases such as 4-dimethylaminopyridine (4-DMAP), 1,8-diazabicyclo[5.4.0]-7-undecene (DBU), etc.; weakly basic ion exchange resins such as Amberlite-93®, Amberlist-21®, Amberlist-93®, etc., among which alkali metal hydroxides and carbonates such as those of lithium, sodium and potassium are preferably used. The acid used for hydrolysis includes mineral acids such as hydrochloric acid, sulfuric acid and phosphoric acid, of which hydrochloric acid is preferably used.

In this manner, the starting material hydroxylamine or a salt thereof is converted into the hydroxamic acid (II) and then the substituted hydroxamic acid (III). Subsequent alkali or acid hydrolysis is carried out in which the molar ratio of a base or an acid to hydroxylamine or a salt thereof is usually 0.1 to 10, preferably 0.5 to 5.

The solvent used for hydrolysis may be an aqueous solution, usually water solely, or a mixed solvent containing water, i.e., consisting of water and a water-soluble organic solvent including alcohols such as methanol, ethanol, etc., and cyclic ethers such as tetrahydrofuran, dioxane, etc. The amount of water used is usually 0.1 to 50 parts, preferably 0.1 to 20 parts, relative to 1 part of the substituted hydroxamic acid (III) by weight. The amount of organic solvent to be mixed with water is usually 0.1 to 10 parts relative to 1 part of water by weight.

Hydrolysis is carried out usually for 1 to 20 hours in the presence of an acid or base at a temperature of 25 to 120° C. For acid hydrolysis, the reaction solution is adjusted to pH 7 or more after the reaction, to give the substituted amine (IV) which is then distilled and isolated. In alkali hydrolysis, the substituted amine (IV) is distilled away as product as the reaction proceeds, so the product can be easily recovered by cooling.

The substituted amine (IV) thus obtained is used preferably as an aqueous solution of sulfuric acid or hydrochloric acid or as sulfate or hydrochloride for easier handling.

The process of the invention permits substituted amines such as alkoxyalkylamine, alkoxyamine, etc., which were produced in low yield in the conventional process, to be produced in higher yield at lower costs with less environmental pollution.

The present invention further provides a method for purifying a N,O-disubstituted hydroxamic acid and/or an O-substituted hydroxamic acid, wherein a mixture containing a N,O-disubstituted hydroxamic acid represented by the general formula (V):

(wherein $R^5$ represents a hydrogen atom or a hydrocarbon group, and $R^6$ and $R^7$ represent a hydrocarbon group or a heteroatom-containing hydrocarbon group) or a mixture containing said N,O-disubstituted hydroxamic acid and an O-substituted hydroxamic acid represented by the general formula (VI):

(wherein $R^5$ and $R^7$ possess the same meanings as defined above) is distilled with water, so that said N,O-disubstituted hydroxamic acid is separated as an azeotropic distillate with water from said mixture.

Examples of hydrocarbon groups represented by $R^5$, $R^6$ or $R^7$ in the formulae (V) and (VI) are $C_1$–$C_5$ alkyl groups, such as methyl group, ethyl group, n-propyl group, isopropyl group, n-butyl group, isobutyl group, sec-butyl group, tert-butyl group, n-pentyl group, etc.; $C_2$–$C_5$ alkenyl groups, such as allyl group etc.; $C_3$–$C_7$ cycloalkyl groups, such as cyclopropyl group, cyclobutyl group, cyclopentyl group, cyclohexyl group, cycloheptyl group, etc.; aryl groups, such as phenyl group, tolyl group, xylyl group, etc.; aralkyl groups, such as benzyl group, phenethyl group, etc.; and aryl-$C_2$–$C_5$-alkenyl groups, such as 3-phenyl-2-propenyl group, etc.

Examples of heteroatom-containing hydrocarbon groups represented by $R^6$ or $R^7$ in the formulae (V) and (VI) are halogenated hydrocarbon groups, such as fluoromethyl group, chloromethyl group, 3-chloroallyl group, 4-chlorobenzyl group, etc.; carbonylated alkyl groups, such as carboxymethyl group, ethoxycarbonylmethyl group, 1-carboxy-1-methylethyl group, etc.; and cyanoalkyl groups, such as cyanomethyl group, cyanoethyl group, etc.

The N,O-disubstituted hydroxamic acid represented by the formula (V) is preferably an N,O-dialkylhydroxamic acid represented by the general formula (V'):

(V')

(wherein R⁵' represents a hydrogen atom or an alkyl group, and R⁶' and R⁷' represent alkyl groups), and the O-substituted hydroxamic acid represented by the formula (VI) is preferably an O-alkylhydroxamic acid represented by the general formula (VI'):

$$R^{5'}CONHOR^{7'} \quad (VI')$$

wherein R⁵' and R⁷' possess the same meanings as defined above.

Examples of alkyl groups represented by R⁵', R⁶' and R⁷' in the above formulae (V') and (VI') are $C_1$–$C_5$ alkyl group, such as methyl group, ethyl group, n-propyl group, isopropyl group, n-butyl group, isobutyl group, sec-butyl group, tert-butyl group, n-pentyl group, etc.

A reaction mixture subjected to the process of the invention is produced by allowing a hydroxylamine salt such as hydroxylamine sulfate to react in the presence of a base such as sodium hydroxide etc. with an ester represented by the general formula (I');

$$R^{5'}COOR^4 \quad (I')$$

(wherein R⁵' possesses the same meaning as defined above, and R⁴ represents a hydrocarbon group) which is then allowed to react with an alkylating agent such as dialkyl sulfates, alkyl bromides, etc. The reaction mixture thus obtained contains a N,O-dialkylhydroxamic acid. Where the molar ratio of the alkylating agent to hydroxylamine or a salt thereof is 2 or more, a N,O-dialkylhydroxamic acid occurs as the major product, and where the molar ratio is 0.5 to 1.5, an O-alkylhydroxamic acid occurs as the major product. The N,O-dialkylhydroxamic acid and O-alkylhydroxamic acid are useful as the starting materials for N,O-dialkylhydroxylamine and O-alkylhydroxylamine, respectively.

In the conventional process, the N,O-dialkylhydroxamic acid was extracted by adding an organic solvent such as chloroform, methylene chloride, dichloroethane, etc., to the above reaction mixture, followed by isolation thereof by fractional distillation.

Examples of hydrocarbon groups represented by R⁴ in the above formula (I') are $C_1$–$C_5$ alkyl groups, such as methyl group, ethyl group, n-propyl group, isopropyl group, n-butyl group, isobutyl group, sec-butyl group, tert-butyl group, n-pentyl group, etc.; $C_3$–$C_7$ cycloalkyl groups, such as cyclopropyl group, cyclobutyl group, cyclopentyl group, cyclohexyl group, cycloheptyl group, etc.; aryl groups such as phenyl group, tolyl group, xylyl group, etc.; and aralkyl groups such as benzyl group, phenethyl group, etc.

Hereinafter, the present invention is described more specifically, but the scope of the present invention is not limited by the conditions described below.

The present invention relates to the production of N,O-disubstituted hydroxamic acid and/or O-substituted hydroxamic acid, comprising separation of N,O-disubstituted hydroxamic acid by azeotropic distillation with water from a solution, in the presence of an amount of water necessary for azeotropic distillation, usually in the presence of an amount of water necessary to produce an azeotropic distillate of water and N,O-disubstituted hydroxamic acid, more specifically the amount of water being usually 5 to 20 parts or more, preferably 11 to 15 parts relative to 1 part of N,O-disubstituted hydroxamic acid by weight under normal pressure or reduced pressure.

For azeotropic distillation, an amount of water (including the water present in the mixture) necessary to constitute an azeotropic mixture is allowed to be present at the time of distillation. Usually, the mixture is a homogeneous system containing organic and inorganic compounds such as alcohols etc., but may be a heterogeneous system containing other organic and inorganic compounds.

A distillation apparatus for the azeotropic mixture is the one equipped with distillation columns capable of precision distillation (e.g. older show distillation columns). For example, an apparatus capable of selectively recovering only the azeotropic distillate is preferably used, but a batch or continuous apparatus capable of recovering other compounds simultaneous with the azeotropic distillate can also be used.

Distillation may be conducted under normal pressure, applied pressure or reduced pressure, preferably under normal pressure or reduced pressure in the range of 1 to 760 mmHg, more preferably 10 to 250 mmHg. The distillation temperature is the azeotropic point of the product and water under a predetermined pressure, preferably in the range of 20 to 160° C., more preferably 30 to 80° C., but a temperature of higher than the azeotropic point of the product and water under a predetermined pressure may also be adopted.

The purification method of the present invention permits the intermediates N,O-dialkylhydroxamic acid and O-alkylhydroxamic acid to be separated from each other more safely and easily than the conventional method, so that N,O-dialkylhydroxylamine and/or O-alkylhydroxylamine can be efficiently produced as final product of high purity.

DESCRIPTION OF THE PREFERRED EMBODIMENTS

The present invention is described in more detail with reference to the following examples, which however are not intended to limit the scope of the present invention.

EXAMPLE 1

(1) 8.2 g (95 mmol) of 95% hydroxylamine sulfate (calculated using the molecular weight of 82.07 for $NH_2OH \cdot (H_2SO_4)\frac{1}{2}$; Hereinafter the same) and 25 ml water were introduced into a 200-ml four-necked flask under a nitrogen atmosphere equipped with a pH electrode, a thermometer, an injector and a pipe for receiving a feed pump, and the mixture was dissolved by stirring with a magnetic stirrer. The inside temperature was cooled to 5° C. Then, 50% aqueous sodium hydroxide was added dropwise thereto until the reaction solution reached pH 10.5. With the inside temperature kept at 5–10° C. and the reaction solution at pH 10.5, 9.5 g of 99.5% ethyl acetate (108 mmol) and 50% aqueous sodium hydroxide were simultaneously added thereto for 40 min. After the addition, stirring was continued for 4 hours under the same conditions.

(2) Then, while the reaction temperature was kept at 5–10° C. and the reaction solution was kept at pH 12.5, 27.8 g (209 mmol) of 95% dimethyl sulfate and 50% aqueous sodium hydroxide were simultaneously added thereto for 1 hour. After the addition, stirring was continued for further 3 hours under the same conditions, and then 22 g of aqueous saturated sodium bicarbonate was added thereto and stirred for 30 min. at an elevated temperature of 50° C. to effect hydrolysis of an excess amount of dimethyl sulfate. Then, the reaction solution was distilled under normal pressure, to give 43 g liquid containing N,O-dimethylacetohydroxamic acid. Analysis of the liquid by gas chromatography indicated that N,O-dimethylacetohydroxamic acid was formed in 84% yield.

(3) The liquid obtained by distillation was introduced into a three-necked 100-ml flask equipped with a distillation column with a cooling unit and was then heated at 50° C. 14 g of 50% aqueous sodium hydroxide was added dropwise thereto for 15 min. for hydrolysis, so that 46 g liquid containing methoxymethylamine (referred to hereinafter as "MMA") distilled through the distillation column was obtained. Quantitative analysis of the liquid by gas chromatography indicated that methoxymethylamine was formed in 84% overall yield.

EXAMPLE 2

The same procedure as in Example 1 was followed except that the synthesis of acetohydroxamic acid in (1) above was conducted at pH 11.5 and the methylation in (2) above was conducted at pH 12.5. As a result, methoxymethylamine was formed in 81% yield.

EXAMPLES 3–8

The same procedure as in Example 1 was followed except that ethyl acetate was replaced by an ester shown in Table 1. The results are also shown in Table 1.

TABLE 1

| Example | ester | MMA yield (%) |
| --- | --- | --- |
| 3 | ethyl formate | 81 |
| 4 | methyl acetate | 83 |
| 5 | isopropyl acetate | 84 |
| 6 | n-butyl acetate | 83 |
| 7 | phenyl acetate | 81 |
| 8 | methyl benzoate | 77 |

EXAMPLE 9

The same procedure as in Example 1 was followed except that sodium hydroxide used in hydrolysis (3) above was replaced by 14 g (143 mmol) of conc. hydrochloric acid. The resulting reaction mixture was evaporated to dryness, whereby methoxymethylamine hydrochloride was obtained in 83% yield.

EXAMPLES 10–12

The same procedure as in Example 1 was followed except that dimethyl sulfate as the alkylating agent was replaced by a reagent shown in Table 2. The results are also shown in Table 2.

TABLE 2

| Example | alkylating reagent[a] | product | yield (%) |
| --- | --- | --- | --- |
| 10 | methyl iodide | methoxymethylamine | 78 |
| 11 | diethyl sulfate | ethoxyethylamine | 81 |
| 12 | butyl iodide | butoxybutylamine | 65 |

[a]molar ratio: alkylating agent/hydroxylamine salt = 2.2

EXAMPLE 13

8.37 g (100 mmol) of 95% hydroxylamine sulfate and 28 ml water were introduced into a 200-ml four-necked flask under a nitrogen atmosphere equipped with a pH electrode connected to a pH controller, a pipe for receiving a feed pump controlled by the pH controller, a thermometer and a dropping funnel. The mixture was dissolved by stirring with a magnetic stirrer and the inside temperature was cooled to 5° C. Then, 50% aqueous sodium hydroxide was added dropwise thereto through the feed pump controlled by the pH controller until the reaction solution reached pH 10.5. With the temperature in the flask kept at 5–10° C. and the reaction solution kept at pH 10.5–10.6, 9.79 g (109 mmol) of 99.5% ethyl acetate was introduced through the dropping funnel for 1 hour simultaneously with the introduction of 50% aqueous sodium hydroxide through the feed pump controlled by the pH controller. After the addition, the solution was stirred for 4 hours at room temperature while the pH was kept at 10.5–10.6. Then, while the reaction temperature was kept at 5–10° C. and the reaction solution at pH 12.5–12.7, 13.97 g (105 mmol) of 95% dimethyl sulfate and 50% aqueous sodium hydroxide were simultaneously added thereto for 1.5 hours. After the addition, the solution was stirred for further 3 hours under the same conditions. Quantitative analysis of the reaction solution by high performance liquid chromatography indicated that O-methylacetohydroxamic acid was formed in 90% yield and N,O-dimethylacetohydroxamic acid in 1% yield. The reaction solution was adjusted within pH 9–10 with aqueous saturated sodium bicarbonate, and N,O-dimethylacetohydroxamic acid as by-product and impurities of low melting point were removed by azeotropic distillation with water under reduced pressure (100 to 120 mmHg). Analysis of the aqueous phase revealed the absence of N,O-dimethylacetohydroxamic acid. 98% sulfuric acid (14.5 g, 150 mmol) was added to the aqueous phase and the solution was stirred at 80° C. for 3 hours. Thereafter, the reaction solution was adjusted in the range of pH 7 or more with 50% aqueous sodium hydroxide and distilled under normal pressure, to give a methoxyamine-containing liquid. Quantitative analysis of the liquid by gas chromatography indicated that methoxyamine was formed in 85% overall yield. 4.17 g (43 mmol) of conc. sulfuric acid was added to the distilled product, and then methanol, ethanol, etc., were distilled off under reduced pressure whereby an aqueous solution of methoxyamine in sulfuric acid was obtained.

EXAMPLES 14–16

The same reaction as in Example 13 was followed except that the methylation of acetohydroxamic acid was carried at a different pH value. The results are shown in Table 3.

TABLE 3

| Example | methylation pH | methoxyamine yield (%) |
| --- | --- | --- |
| 14 | 9.5 | 75 |
| 15 | 10.5 | 82 |
| 16 | 11.5 | 80 |
| 13 | 12.5–12.7 | 85 |

EXAMPLE 17

An aqueous solution containing methoxyamine was distilled in the same manner as in Example 13, and 16.8 g (170 mmol) of conc. hydrochloric acid was then added thereto, and the reaction solution was evaporated to dryness under reduced pressure, whereby 7.1 g methoxyamine hydrochloride was obtained.

EXAMPLE 18

Acetohydroxamic acid was allowed to react with dimethyl sulfate in the same manner as in Example 13, and after the by-product N,O-dimethylhydroxamic acid was removed by washing it with toluene, O-methylacetohydroxamic acid was extracted with isopropanol. The extraction solvent was distilled off under reduced pressure, and the distillation of the sample solution under reduced pressure (b.p.=70° C./0.05 torr.) brought about 6.23 g O-methylacetohydroxamic acid (72 mmol, 72% yield). After addition of conc. hydrochloric acid (6.9 g, 72 mmol), this product was allowed to react at 80° C. for 3 hours and then evaporated to dryness under reduced pressure to form 5.9 g methoxyamine hydrochloride.

EXAMPLE 19

The same procedure as in Example 14 was followed except that hydrolysis was carried out with sodium hydroxide in place of conc. hydrochloric acid. Distillation of the reaction mixture gave 3.06 g methoxyamine (65% yield).

EXAMPLES 20–27

The same procedure as in Example 13 was followed except that ethyl acetate was replaced by an ester shown in Table 4. The results are also shown in Table 4.

TABLE 4

| Example | ester | methoxyamine yield (%) |
|---|---|---|
| 20 | ethyl formate | 78 |
| 21 | methyl acetate | 83 |
| 22 | isopropyl acetate | 84 |
| 23 | n-butyl acetate | 83 |
| 24 | phenyl acetate | 75 |
| 25 | methyl propionate | 79 |
| 26 | ethyl butyrate | 79 |
| 27 | methyl benzoate | 77 |

EXAMPLES 28–36

The same procedure as in Example 13 was followed except that a reagent shown in Table 5 was used in place of dimethyl sulfate as the alkylating agent. The results are also shown in Table 5.

TABLE 5

| Example | alkylating reagent [a] | product | yield (%) |
|---|---|---|---|
| 28 | diethyl sulfate | ethoxyamine | 80 |
| 29 | methyl chloride | methoxyamine | 75 |
| 30 | n-propyl iodide | n-propoxyamine | 71 |
| 31 | isopropyl iodide | isopropoxyamine | 62 |
| 32 | n-butyl iodide | n-butoxyamine | 65 |
| 33 | allyl chloride | allyloxyamine | 70 |
| 34 | 4-chlorobenzyl chloride | 4-chlorobenzyloxyamine | 74 |
| 35 | ethyl 1-chloroacetate | ethoxycarbonylmethyloxyamine | 75 |
| 36 | chloroacetonitrile | cyanomethyloxyamine | 70 |

[a] mole ratio: alkylating agent/hydroxylamine salt = 1.05

EXAMPLE 37

8.2 g (95 mmol) of 95% hydroxylamine sulfate (calculated using the molecular weight of 82.07 for $NH_2OH \cdot (H_2SO_4)_{1/2}$) and 25 ml water were introduced into a four-necked 200-ml flask under a nitrogen atmosphere equipped with a pH electrode, a thermometer and a pipe for receiving a feed pump. The mixture was dissolved by stirring with a magnetic stirrer, and the inside temperature was cooled to 5° C. Then, 50% aqueous sodium hydroxide was added dropwise thereto until the reaction solution reached pH 11.5. While the inside temperature was kept at 5–10° C. and the reaction solution was kept at pH 10.5–11.0, 9.5 g of 99.5% ethyl acetate (108 mmol) and 50% aqueous sodium hydroxide were simultaneously added thereto for 40 min. After the addition, stirring was continued for 4 hours under the same conditions. Then, while the reaction temperature was kept at 5–10° C. and the reaction solution was kept at pH 12.5–13, 27.8 g (209 mmol) of 95% dimethyl sulfate and 50% aqueous sodium hydroxide were simultaneously added thereto for 1 hour. After the addition, stirring was continued for further 3 hours under the same conditions, and then 22 g of aqueous saturated sodium bicarbonate was added thereto and stirred at an elevated temperature of 50° C. for 30 min. to effect hydrolysis of an excess amount of dimethyl sulfate and then cooled to room temperature. Quantitative analysis of the reaction solution by gas chromatography indicated that N,O-dimethylacetohydroxamic acid was formed in 85% yield and O-methylacetohydroxamic acid in 3% yield. Then, after the flask was provided with 5-stages older show distillation columns, the reaction solution was subjected to distillation under a reduced pressure of 50–80 mmHg, so that a distillate of boiling point of 40 to 50° C. was obtained. When about ⅔ of the total volume was distilled, 100 ml water was added thereto. Further distillation brought about finally 153 g of an azeotropic distillate with water containing methanol, ethanol and N,O-dimethylacetohydroxamic acid (5.2% purity: 81.6% yield after isolation). No O-methylacetohydroxamic acid was contained as impurity in the azeotropic distillate. Hydrolysis of the azeotropic distillate with an acid or a base yielded the final product N,O-dimethylhydroxylamine quantitatively.

EXAMPLE 38

The same reaction and distillation as in Example 37 were carried out except that the by-product, O-methylacetohydroxamic acid, was allowed to coexist before distillation in an amount of approximately 10% relative to N,O-dimethylacetohydroxamic acid. As a result, 151 g of an azeotropic distillate with water containing methanol and ethanol and N,O-dimethylacetohydroxamic acid (5.5% purity: 82.5% yield after isolation) was obtained. No O-methylacetohydroxamic acid was contained as impurity in the azeotropic distillate.

EXAMPLE 39

The same procedure as in Example 37 was followed except that normal pressure was adopted for distillation in place of the reduced pressure of 50 to 80 mmHg. As a result, 160 g of an azeotropic distillate with water containing methanol, ethanol and N,O-dimethylacetohydroxamic acid (5.2% purity: 80% yield after isolation) was obtained as a distillate of boiling point of 90 to 105° C. No O-methylhydroxamic acid was contained as impurity in the azeotropic distillate.

EXAMPLE 40

58.62 g (700 mmol) of 98% hydroxylamine sulfate and 100 ml water were introduced into a 500-ml four-necked flask under a nitrogen atmosphere equipped with a pH electrode connected to a pH controller, a pipe for receiving a feed pump controlled by the pH controller, a thermometer and a dropping funnel. The mixture was dissolved by stirring with a mechanical stirrer and the inside temperature was cooled to 5° C. Then, 50% aqueous sodium hydroxide was added dropwise thereto through the feed pump controlled by the pH controller until the reaction solution reached pH 10.0. With the temperature in the flask kept at 5–10° C. and the reaction solution kept at pH 10.0–10.3, 65.4 g (735 mmol) of 99.5% ethyl acetate was introduced through the dropping funnel for 1 hour simultaneously with the introduction of 50% aqueous sodium hydroxide through the feed pump controlled by the pH controller. After the addition, the solution was stirred for 4 hours at room temperature while the pH was kept at 10.5–10.6. Then, while the reaction temperature was kept at 5–10° C. and the reaction solution at pH 9.5–9.7, 97.6 g (735 mmol) of 95% dimethyl sulfate and 50% aqueous sodium hydroxide were simultaneously added thereto for 1.5 hours. After the addition, the solution was stirred for further 3 hours under the same conditions. Quantitative analysis of the reaction solution by high performance liquid chromatography indicated that O-methylacetohydroxamic acid was formed in 92% yield and N,O-dimethylacetohydroxamic acid in 5.6% yield. N,O-dimethylacetohydroxamic acid as by-product and impurities of low melting point were removed by azeotropic distillation with water under reduced pressure (100 to 120 mmHg). 98% sulfuric acid (59.5 g, 595 mmol) was added to the aqueous phase and the solution was stirred at 80° C. for 3 hours. Thereafter, the reaction solution was adjusted at pH 13.5 with 50% aqueous sodium hydroxide and distilled under reduced pressure (80–120 mmHg), to give a methoxyamine-containing liquid. Quantitative analysis of the liquid by gas chromatography indicated that methoxyamine was formed in 86.5% overall yield. 29.2 g (298 mmol) of conc. sulfuric acid was added to the distilled product, and then methanol, ethanol, etc., were distilled off under reduced pressure whereby an aqueous solution of methoxyamine in sulfuric acid was obtained.

What is claimed is:

1. A process for producing a substituted amine represented by the general formula (IV-a):

wherein $R^3$ represents a hydrocarbon group or a heteroatom-containing hydrocarbon group, which comprises the steps of:

(b) reacting a hydroxamic acid represented by the general formula (III):

wherein $R^1$ represents a hydrogen atom or a hydrocarbon group, in the presence of a base with a dialkyl sulfate or a halide represented by the formula $R^3$—X, wherein X represents a halogen atom to form a N,O-disubstituted hydroxamic acid represented by the general formula (III-a):

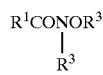

wherein $R^1$ represents a hydrogen atom or a hydrocarbon group, $R^3$ represents a hydrocarbon group or a heteroatom-containing hydrocarbon group, and said N,O-disubstituted hydroxamic acid is hydrolyzed in the presence of a base to produce a disubstituted amine represented by the general formula (IV-a):

2. A process for producing a substituted amine according to claim 1, wherein the dialkyl sulfate or halide represented by the formula $R^3$—X, wherein X represents a halogen atom is an alkylating agent selected from the group consisting of a dialkyl sulfate, alkyl chloride, alkyl bromide and alkyl iodide, the N,O-disubstituted hydroxamic acid is a N,O-dialkylhydroxamic acid, and the disubstituted amine obtained by hydrolysis thereof is an alkoxyalkylamine.

3. A process for producing a substituted amine according to claim 1, wherein the dialkyl sulfate or halide represented by the formula $R^3$—X, wherein X represents a halogen atom, is an alkylating agent selected from the group consisting of a dialkyl sulfate, alkyl chloride, alkyl bromide and alkyl iodide.

4. A process for producing a substituted amine according to claim 1, which comprises the steps of:

(a) reacting hydroxylamine or a salt thereof in the presence of a base with an ester represented by the general formula (I):

wherein $R^1$ represents a hydrogen atom or a hydrocarbon group, and $R^4$ represents a hydrocarbon group, to produce a reaction mixture containing a hydroxamic acid represented by the general formula (II):

(b) reacting said hydroxamic acid-containing reaction mixture in the presence of a base without separation, of the hydroxamic acid from said mixture, with an alkylating agent selected from the group consisting of a dialkyl sulfate, alkyl chloride, alkyl bromide and alkyl iodide, at the molar ratio of the alkylating agent to hydroxylamine or a salt thereof being from 2 to 4, which, in the case of the salt, is calculated not from the number of moles of the salt itself but from the number of moles of hydroxylamine contained in said salt, to produce a N,O-dialkylhydroxamic acid represented by the general formula (III-a'):

wherein $R^3$ represents an alkyl group, and (c) hydrolyzing said N,O-dialkylhydroxamic acid in the presence of a base to produce an alkoxyalkylamine represented by the general formula (IV-a'):

5. A process for producing a substituted amine according to claim 1, wherein a mixture containing a N,O-disubstituted hydroxamic acid represented by the general formula (III-a);

and an O-substituted hydroxamic acid represented by the general formula (III-b):

is distilled with water to separate the N,O-disubstituted hydroxamic acid represented by the general formula (III-a):

$$R^1CONOR^3 \atop | \atop R^3 \qquad (III\text{-}a)$$

as an azeotropic distillate with water from said mixture, and said N,O-disubstituted hydroxamic acid is hydrolyzed in the presence of a base or an acid to produce a disubstituted amine represented by the general formula (IV-a);

$$R^3NOR^3 \qquad (IV\text{-}a).$$

6. A process for producing a substituted amine represented by the general formula (IV-b):

$$H_2NOR^3 \qquad (IV\text{-}b)$$

wherein $R^3$ represents a hydrocarbon group or a hetero atom-containing hydrocarbon group, which comprises the steps of reacting a hydroxamic acid represented by the general formula (II):

$$R^1CONHOH \qquad (II),$$

wherein $R^1$ represents a hydrogen atom or a hydrocarbon group in the presence of a base with a dialkyl sulfate or a halide represented by the formula $R^3$—X, wherein X represents a halogen atom to form an O-substituted hydroxamic acid represented by the general formula (III-b):

$$R^1CONHOR^3 \qquad (III\text{-}b)$$

wherein $R^1$ represents a hydrogen atom or a hydrocarbon group, $R^3$ represents a hydrocarbon group or a heteroatom-containing hydrocarbon group and hydrolyzing said O-substituted hydroxamic acid in the presence of a base to produce a monosubstituted amine represented by the general formula (IV-b):

$$H_2NOR^3 \qquad (IV\text{-}b).$$

7. A process for producing a substituted amine according to claim 6, wherein the dialkyl sulfate or halide represented by the formula $R^3$—X, wherein X represents a halogen atom is an alkylating agent selected from the group consisting of a dialkyl sulfate, alkyl chloride, alkyl bromide and alkyl iodide, the O-substituted hydroxamic acid is an O-alkylhydroxamic acid, and the monosubstituted amine obtained by hydrolysis thereof is an alkoxyamine.

8. A process for producing a substituted amine represented by the general formula (IV-b'):

$$H_2NOR^3 \qquad (IV\text{-}b')$$

wherein $R^3$ represents an alkyl group, which comprises the steps of:

(a) reacting hydroxylamine or a salt thereof in the presence of a base with an ester represented by the general formula (I):

$$R^1COOR^4 \qquad (I)$$

wherein $R^1$ represents a hydrogen atom or a hydrocarbon group, and $R^4$ represents a hydrocarbon group, to produce a reaction mixture containing a hydroxamic acid represented by the general formula (II):

$$R^1CONHOH \qquad (II),$$

(b) reacting said hydroxamic acid-containing reaction mixture in the presence of a base without separation of the hydroxamic acid from said mixture, with an alkylating agent selected from the group consisting of a dialkyl sulfate, alkyl chloride, alkyl bromide and alkyl iodide, at the molar ratio of the alkylating agent to hydroxylamine or a salt thereof being from 0.5 to 1.5, which, in the case of the salt, is calculated not from the number of moles of the salt itself but from the number of moles of hydroxylamine contained in said salt, to produce an O-alkylhydroxamic acid represented by the general formula (III-b'):

$$R^1CONHOR^3 \qquad (III\text{-}b')$$

wherein $R^3$ represents an alkyl group, and (c) hydrolyzing said O-alkylhydroxamic acid in the presence of a base to produce an alkoxyalkylamine represented by the general formula (IV-b'):

$$H_2NOR^{3'} \qquad (IV\text{-}b').$$

9. A method for purifying a N,O-disubstituted hydroxamic acid and/or an O-substituted hydroxamic acid, which comprises distilling a mixture containing a N,O-disubstituted hydroxamic acid represented by the general formula (V):

$$R^5CONOR^7 \atop | \atop R^6 \qquad (V)$$

wherein $R^5$ represents a hydrogen atom or a hydrocarbon group, and $R^6$ and $R^7$ represent a hydrocarbon group or a heteroatom-containing hydrocarbon group, or a mixture containing said N,O-disubstituted hydroxamic acid and an O-substituted hydroxamic acid represented by the general formula (VI)

$$R^5CONHOR^7 \qquad (VI)$$

with water to separate said N,O-disubstituted hydroxamic acid as an azeotropic distillate with water from said mixture.

10. A method according to claim 9, wherein the N,O-disubstituted hydroxamic acid is a N,O-dialkylhydroxamic acid represented by the general formula (V'):

$$R^{5'}CONOR^{7'} \atop | \atop R^{6'} \qquad (V')$$

wherein $R^{5'}$ represents a hydrogen atom or an alkyl group, and $R^{6'}$ and $R^{7'}$ represent alkyl groups, and the O-substituted hydroxamic acid is an O-alkylhydroxamic acid represented by the general formula (VI'):

$$R^{5'}CONHOR^{7'} \qquad (VI').$$

11. A method according to claim 10, wherein said N-O-dialkylhydroxamic acid is purified.

12. A method according to claim 10, wherein a mixture containing said N,O-dialkylhydroxamic acid and said O-alkylhydroxamic acid is distilled with water to separate said N,O-dialkylhydroxamic acid as an azeotropic distillate with water from said mixture in order to purify said O-alkylhydroxamic acid.

13. A method according to claim 10, wherein said N,O-dialkylhydroxamic acid is N,O-dimethylacetohydroxamic acid.

14. A process according to claim 10, wherein said O-alkylhydroxamic acid is O-methylacetohydroxamic acid.

* * * * *